(12) United States Patent
Okamura

(10) Patent No.: US 9,248,264 B2
(45) Date of Patent: Feb. 2, 2016

(54) DILATOR, INTRODUCER ASSEMBLY, AND MEDICAL TOOL

(71) Applicant: TERUMO KABUSHIKI KAISHA, Shibuya-ku (JP)

(72) Inventor: Ryo Okamura, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/167,323

(22) Filed: Jan. 29, 2014

(65) Prior Publication Data

US 2014/0180211 A1 Jun. 26, 2014

Related U.S. Application Data

(63) Continuation of application No. PCT/JP2012/069363, filed on Jul. 30, 2012.

(30) Foreign Application Priority Data

Aug. 1, 2011 (JP) .................................. 2011-168774

(51) Int. Cl.
*A61M 29/00* (2006.01)
*A61M 25/06* (2006.01)

(52) U.S. Cl.
CPC ............ *A61M 29/00* (2013.01); *A61M 25/0606* (2013.01); *A61M 25/0662* (2013.01); *A61M 2025/0681* (2013.01)

(58) Field of Classification Search
CPC ..................... A61M 25/0662; A61M 25/0606; A61M 2025/0681; A61M 29/00
USPC .......................... 604/104, 164.01, 164.1, 525
See application file for complete search history.

(56) References Cited

U.S. PATENT DOCUMENTS 4,978,334 A 12/1990 Toye et al.
5,976,146 A 11/1999 Ogawa et al.
(Continued)

FOREIGN PATENT DOCUMENTS

JP 6-335531 A 6/1994
JP 11-76246 A 3/1999
(Continued)

OTHER PUBLICATIONS

International Search Report (PCT/ISA/210) mailed on Nov. 6, 2012, by the Japanese Patent Office as the International Searching Authority for International Application No. PCT/JP2012/069363.
European Communication and Supplementary Search Report dated Feb. 20, 2015 issued in the corresponding European Patent Application No. 12820252.0-1506/2740512 (5 pages).

*Primary Examiner* — Theodore Stigell
*Assistant Examiner* — Amber Stiles
(74) *Attorney, Agent, or Firm* — Buchanan Ingersoll & Rooney PC

(57) ABSTRACT

A dilator includes a first section, a second section, a third section, and a fourth section which have different diameters and are adjacent to each other in an axial direction, an angle formed by an outer peripheral surface of the first section with respect to the axial direction is smaller than an angle formed by an outer peripheral surface of the second section with respect to the axial direction, the angle formed by the outer peripheral surface of the second section with respect to the axial direction is larger than an angle formed by an outer peripheral surface of the third section with respect to the axial direction, and the angle formed by an outer peripheral surface of the third section with respect to the axial direction is smaller than an angle formed by an outer peripheral surface of the fourth section with respect to the axial direction.

15 Claims, 7 Drawing Sheets

(56) References Cited

U.S. PATENT DOCUMENTS

| | | | |
|---|---|---|---|
| 2004/0073141 A1* | 4/2004 | Hartley et al. | 600/585 |
| 2005/0070949 A1* | 3/2005 | Bakos | A61B 1/00154 606/191 |
| 2006/0217664 A1 | 9/2006 | Hattler et al. | |
| 2009/0062735 A1* | 3/2009 | Bartlett | A61B 17/3415 604/104 |
| 2009/0182246 A1* | 7/2009 | Kinoshita et al. | 600/585 |

FOREIGN PATENT DOCUMENTS

| | | |
|---|---|---|
| JP | 2005-329063 A | 12/2005 |
| JP | 2008-011867 A | 1/2008 |
| JP | 2008-11867 A | 1/2008 |

* cited by examiner

US 9,248,264 B2

DILATOR, INTRODUCER ASSEMBLY, AND MEDICAL TOOL

CROSS REFERENCES TO RELATED APPLICATIONS

This application claims priority as a continuation application under 35 U.S.C. §120 to International Application No. PCT/JP2012/069363 filed on Jul. 30, 2012, designating the U.S., and claims priority to Japanese Application No. 2011-168774 filed on Aug. 1, 2011, the entire content of both of which is incorporated herein by reference.

TECHNICAL FIELD

The present disclosure relates to a dilator used for diametrical expansion of a hole communicating the outside with the inside of a living body, and an introducer assembly and a medical tool including the dilator.

BACKGROUND DISCUSSION

The Seldinger method is a method of percutaneously introducing a catheter into the inside of a living body, such as into a blood vessel. In the Seldinger method, a hole which communicates the outside with the inside of a living body is formed by puncturing the skin with a needle. Then, a dilator, which has been inserted through the inside of a tubular introducer sheath through which a catheter can be inserted, is inserted into the hole.

The dilator protrudes from a distal end of the introducer sheath, and expands the diameter of the hole with a taper-shaped outer peripheral surface while passing through the hole. Accordingly, an operator senses resistance at the time of inserting the introducer sheath and the dilator into the hole. Here, a proposal is made to decrease the resistance.

In JP-A-2008-11867, for example, to realize decrease of the resistance, puncture resistance at the time when a distal endmost portion of the dilator punctures the hole, and diameter expansion resistance at the time when the dilator passes through the hole and expands the diameter thereof, as the resistances sensed by the operator, are set to be separately applied, rather than being applied substantially at the same time as is generally the case.

SUMMARY

However, although the diameter expansion resistance is set to be applied separately from the puncture resistance in the dilator of JP-A2008-11867, the diameter expansion resistance itself is not decreased, and accordingly, the operator practically still senses great resistance when the dilator passes through the hole and expands the diameter thereof.

The present application discloses a dilator which alleviates diameter expansion resistance which is sensed by an operator at the time of inserting the dilator and accordingly can perform smooth insertion thereof into a hole which communicates the outside with the inside of a living body, and an introducer assembly and a medical tool including such a dilator.

The inventors have found that the resistance sensed by the operator can be alleviated by changing the increase in the diameter expansion resistance in a stepwise manner, in an order of relatively small, large, small, large increase.

That is, there is provided a dilator including a first section, a second section, a third section, and a fourth section which have different diameters from each other and are formed to be adjacent to each other in an axial direction, in that order from a distal end to a proximal end in the axial direction, in which an angle formed by an outer peripheral surface of the first section with respect to the axial direction is smaller than an angle formed by an outer peripheral surface of the second section with respect to the axial direction, the angle formed by the outer peripheral surface of the second section with respect to the axial direction is larger than an angle formed by an outer peripheral surface of the third section with respect to the axial direction, and the angle formed by the outer peripheral surface of the third section with respect to the axial direction is smaller than an angle formed by an outer peripheral surface of the fourth section with respect to the axial direction.

In addition, there is provided an introducer assembly including: a dilator which includes a first section, a second section, a third section, and a fourth section which have different diameters from each other and are formed to be adjacent to each other in an axial direction, in that order from a distal end to a proximal end in the axial direction; and an introducer sheath which includes a lumen into which the dilator can be inserted and a distal portion, in which in the dilator, an angle formed by an outer peripheral surface of the first section with respect to the axial direction is smaller than an angle formed by an outer peripheral surface of the second section with respect to the axial direction, the angle formed by the outer peripheral surface of the second section with respect to the axial direction is larger than an angle formed by an outer peripheral surface of the third section with respect to the axial direction, the angle formed by the outer peripheral surface of the third section with respect to the axial direction is smaller than an angle formed by an outer peripheral surface of the fourth section with respect to the axial direction, and the distal portion of the introducer sheath is disposed at a proximal end side with respect to a proximal end of the fourth section.

In addition, there is provided a medical tool including: a dilator which includes a first section, a second section, a third section, and a fourth section which have different diameters from each other and are formed to be adjacent to each other in an axial direction, in that order from a distal end to a proximal end in the axial direction; and a needle which can form a hole communicating with a body lumen, by puncturing the skin, in which an outer diameter of the first section is smaller than an outer diameter of the needle, an angle formed by an outer peripheral surface of the first section with respect to the axial direction is smaller than an angle formed by an outer peripheral surface of the second section with respect to the axial direction, the angle formed by the outer peripheral surface of the second section with respect to the axial direction is larger than an angle formed by an outer peripheral surface of the third section with respect to the axial direction, and the angle formed by the outer peripheral surface of the third section with respect to the axial direction is smaller than an angle formed by an outer peripheral surface of the fourth section with respect to the axial direction.

According to the dilator configured as described above, if the first section, the second section, the third section, and the fourth section pass through the hole in this order, increase in diameter expansion resistance is changed in a stepwise manner, in an order of relatively small, large, small, large increase, due to differences in the angles formed by the outer peripheral surface of each section with respect to the axial direction, and accordingly, the diameter expansion resistance sensed by an operator is alleviated and thus insertion of the dilator can be smoothly performed.

In addition, if the dilator includes a distal endmost portion which is formed on a distal end side of the first section in the axial direction, in which an outer periphery of the distal endmost portion in a cross section in the axial direction which passes through a shaft center includes a parabola in which a diameter thereof decreases towards a distal end from a proximal end in the axial direction, and which has a convex shape from the shaft center towards the outer side in a radial direction, puncture resistance at the time when the dilator punctures the hole is decreased, and accordingly insertion of the dilator can be smoothly performed.

If the outer diameter of the first section is smaller than an outer diameter of a needle which can form a hole which is inserted into a body lumen by puncturing skin, puncture resistance at the time when the dilator punctures the hole is decreased, and accordingly insertion of the dilator can be smoothly performed.

If the first section and the second section, the second section and the third section, and the third section and the fourth section are connected to each other by curved surfaces, respectively, inclination of the outer peripheral surface of the dilator with respect to the axial direction gently changes from the distal end towards the proximal end in the axial direction, and as a result, resistance generated in a boundary of each section due to difference in inclination of the outer peripheral surface of each section is decreased, and accordingly insertion of the dilator can be smoothly performed.

According to the introducer assembly configured as described above, if the first section, the second section, the third section, and the fourth section pass through the hole in this order, the increase in the diameter expansion resistance changes in a stepwise manner in an order of relatively small, large, small, large increase, based on the differences in angles formed by the outer peripheral surface of each section with respect to the axial direction, and accordingly, the diameter expansion resistance sensed by an operator is alleviated and thus insertion of the dilator can be smoothly performed.

If the length from the distal endmost portion of the distal portion of the introducer sheath to the proximal end of the fourth section is greater than the length of the first section and is smaller than the length of the fourth section, the insertion resistance felt by the hand when the introducer sheath 40 is inserted is reduced.

According to the medical tool configured as described above, if the first section, the second section, the third section, and the fourth section pass through the hole in this order, the increase in the diameter expansion resistance changes in a stepwise manner in an order of relatively small, large, small, large increase, based on the differences in angles formed by the outer peripheral surface of each section with respect to the axial direction, and accordingly, the diameter expansion resistance sensed by an operator is alleviated and thus insertion of the dilator can be smoothly performed.

If the needle and the dilator are accommodated in one package, an operator does not need to prepare the needle and the dilator separately, and an excellent working property is obtained.

DETAILED DESCRIPTION

Hereinafter, embodiments will be described with reference to the drawings. Dimensional ratios of the drawings are magnified and may be different from actual ratios, for convenience of description.

Figure 1:
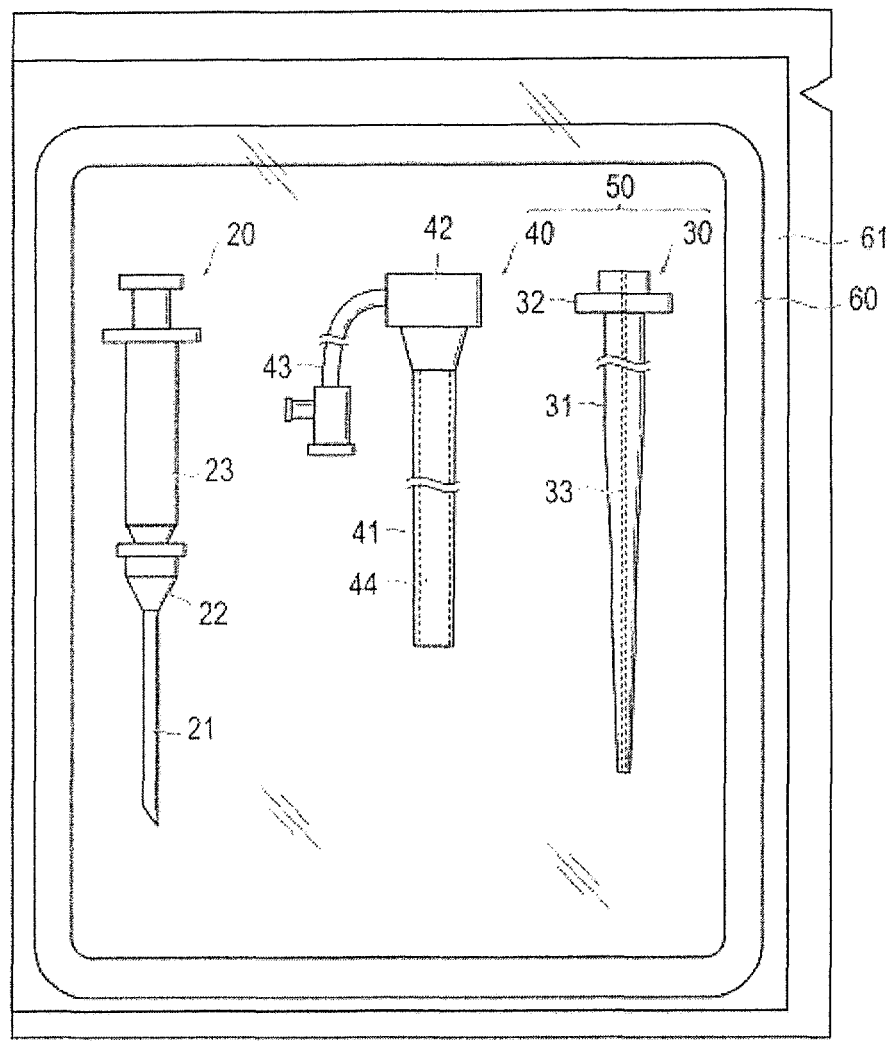
FIG. 1 is a schematic configuration diagram of a medical tool.

To describe FIG. 1, a medical tool 10 of the embodiment includes a puncture tool 20 which forms a hole communicating the outside with the inside of a living body, and an introducer assembly 50 which secures a path through the hole into the inside of the living body.

The medical tool 10 includes a tray 60 on which the puncture tool 20 and the introducer assembly 50 are loaded. In addition, the medical tool 10 includes a package 61 which accommodates the puncture tool 20, the introducer assembly 50, and the tray 60.

The tray 60 is formed of plastic, for example. The package 61 is formed, for example, of a gas-permeable non-woven fabric on which ethylene oxide gas sterilization can preferably be performed, and a film, and the film is formed of, for example, a polyolefin resin such as polyethylene, a polyester resin such as polyethylene terephthalate, or metal foil such as aluminum laminated film.

The puncture tool 20 includes a needle 21 which can form a hole by puncturing the skin, a hub 22 which is fixed to a proximal end of the needle 21, and a syringe 23 which can be attached to and detached from the hub 22.

The needle 21 has a hollow tubular shape, and includes a sharp needle tip at the distal end thereof. The needle 21 is formed by a metal material such as stainless steel, for example. An outer diameter of the needle 21 is, for example, 0.60 mm to 1.80 mm (24 G to 18 G). The needle 21 may have an integrated metallic inner needle and a plastic outer needle which can be separated from each other.

The hub 22 has a hollow shape from a distal end which is fixed to the needle 21, to a proximal end to which the syringe 23 is detachably connected. A material forming the hub 22 is, for example, a resin material such as polyolefin such as polyethylene, polypropylene, or an ethylene-vinyl acetate copolymer, polyvinyl chloride, polybutadiene, polyamide, polyester, or polycarbonate.

The syringe 23 is connected to the hub 22 by fitting a distal end thereof to the proximal end of the hub 22, and communicates with the needle 21 through the hub 22. The syringe 23 is, for example, formed of the resin material which is the same as that of the hub 22 described above. The syringe 23 has optical transparency, and therefore an operator can visually recognize the inside of the syringe 23.

The introducer assembly 50 includes a dilator 30 which expands a hole which communicates the outside of a living body with the inside of the living body, and an introducer sheath 40 which is placed in the expanded hole for communication of the inside and the outside of the living body.

The introducer sheath 40 includes a tubular sheath tube 41 having flexibility, a sheath hub 42 which is fixed to a proximal end of the sheath tube 41, and a liquid injection tube 43 for liquid injection of saline or the like and which communicates with the sheath tube 41 through the sheath hub 42.

The introducer sheath 40 includes, in the sheath tube 41, a lumen 44 into which the dilator 30 can be inserted. The lumen 44 communicates with the inside of the sheath hub 42. The dilator 30 is inserted through the lumen 44 from a proximal end of the sheath hub 42.

The dilator 30 includes an elongated dilator tube 31 having flexibility, and a dilator hub 32 which is fixed to a proximal end of the dilator tube 31. In addition, the dilator 30 includes an inner cavity 33 which extends through the dilator tube 31 and the dilator hub 32 in an axial direction.

Figure 2:
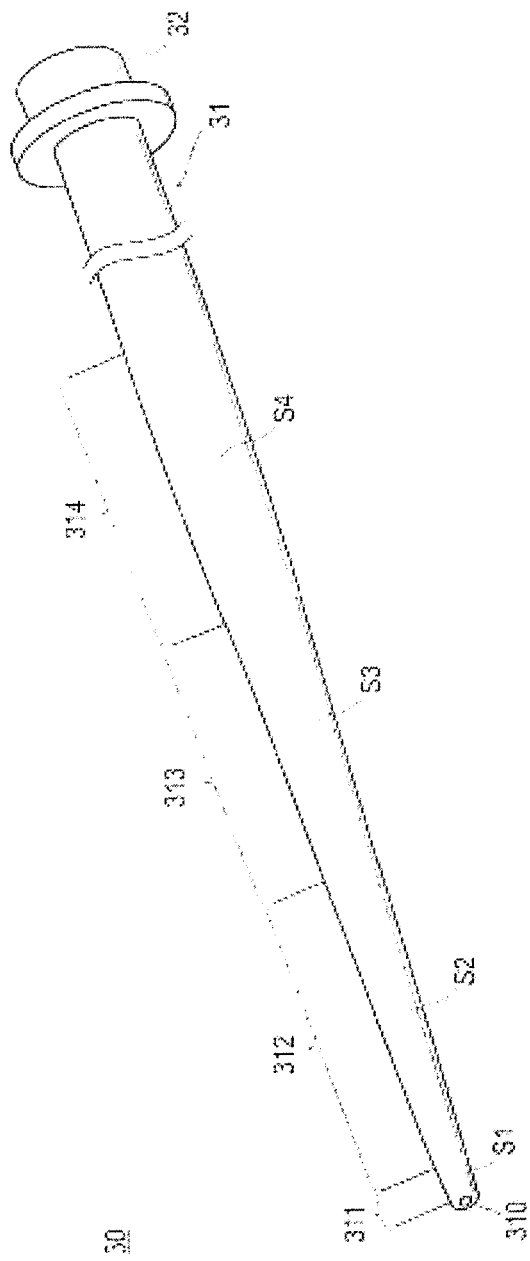
FIG. 2 is a perspective view of a dilator.
Figure 3:
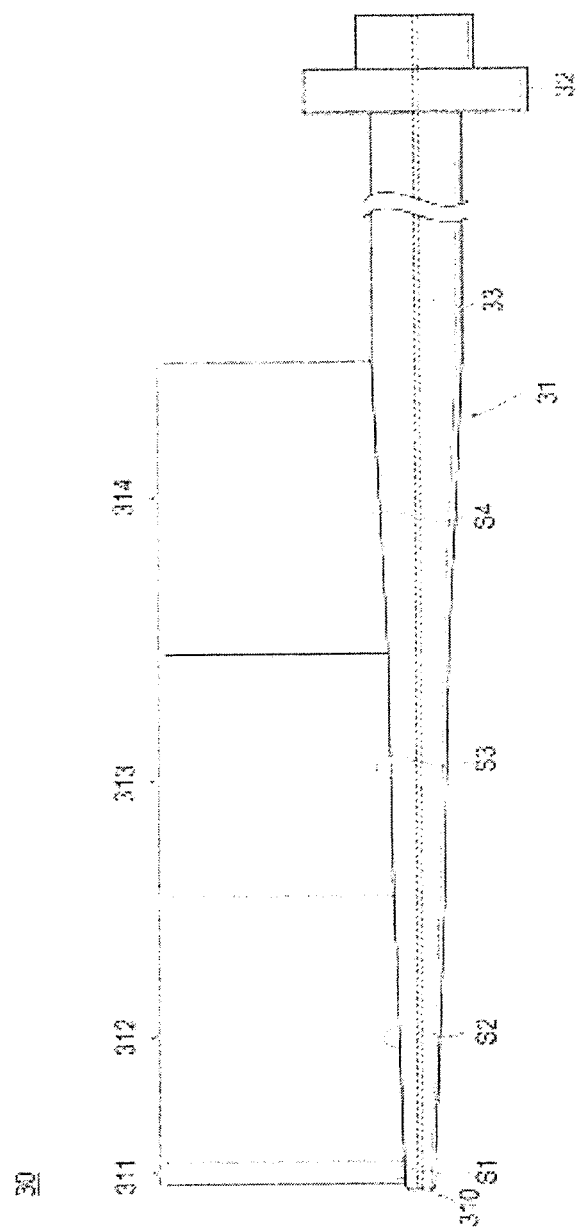
FIG. 3 is a side view of a dilator.

As shown in FIG. 2 and FIG. 3, the dilator tube 31 includes a first section 311, a second section 312, a third section 313, and a fourth section 314 which have different diameters from each other and are formed to be adjacent to each other in an axial direction, in that order from a distal end to a proximal end in the axial direction. In other words, the first section 311 is adjacent to and disposed on a distal side of the second section 312, the second section 312 is adjacent to and disposed on a distal side of the third section 313, and the third section 313 is adjacent to and disposed on a distal side of the fourth section 314. In addition, the dilator tube 31 includes a distal endmost portion 310 which is formed on a distal end of the first section 311 in the axial direction.

A length from the distal endmost portion 310 to a rear end of the fourth section 314 in the axial direction is, for example, 20 mm to 25 mm. In addition, a length of the first section 311 in the axial direction is, for example, 0.1 mm to 5.0 mm. A length of the second section 312 in the axial direction is, for example, 1.0 mm to 30.0 mm. A length of the third section 313 in the axial direction is, for example, 1.0 mm to 30.0 mm. A length of the fourth section 314 in the axial direction is, for example, 1.0 mm to 30.0 mm.

As a configuration material of the dilator tube 31, a polymer material such as polyolefin (for example, polyethylene, polypropylene, polybutene, an ethylene-propylene copolymer, an ethylene-vinyl acetate copolymer, an ionomer, or a mixture of two or more kinds), polyolefin elastomer, a crosslinked body of polyolefin, polyvinyl chloride, polyamide, polyamide elastomer, polyester, polyester elastomer, polyurethane, polyurethane elastomer, a fluorine resin, polycarbonate, polystyrene, polyacetal, polyimide, polyetherimide, or a mixture thereof can be used, for example.

Figure 4:
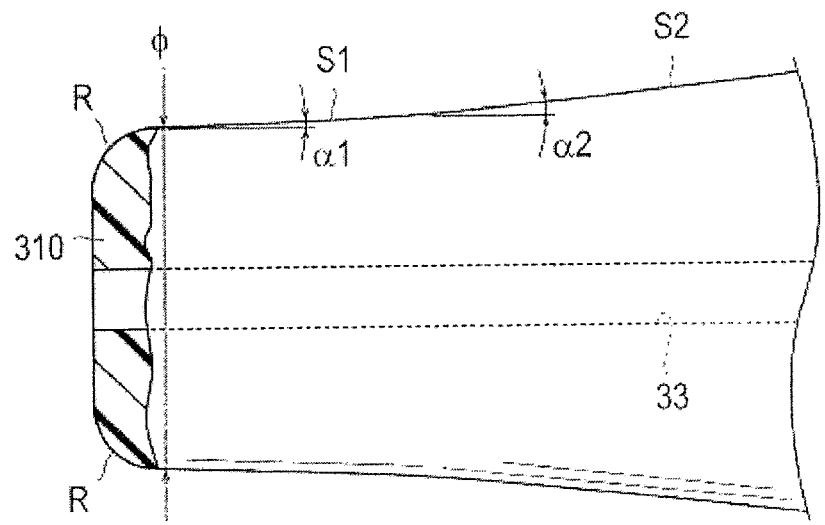
FIG. 4 is a partially enlarged view of a dilator.

As shown in FIG. 4, an outer periphery of the distal endmost portion 310 in a cross section in the axial direction which passes through a shaft center includes a parabola R in which a diameter thereof decreases towards a distal end from a proximal end in the axial direction, and which has a convex shape from the shaft center towards the outer side in a radial direction. In addition, an angle $\alpha 1$ formed by an outer peripheral surface S1 of the first section 311 with respect to the axial direction is smaller than an angle $\alpha 2$ formed by an outer peripheral surface S2 of the second section 312 with respect to the axial direction ($\alpha 1 < \alpha 2$).

The angle $\alpha 1$ is preferably 0° to 10° and more preferably 5°, however it is not limited thereto. In a case where the angle $\alpha 1$ is 0°, the outer peripheral surface S1 has a cylindrical shape having a constant diameter in the axial direction. In addition, in a case where the angle $\alpha 1$ is larger than 0°, the outer peripheral surface S1 has a tapered shape inclined so as to expand in diameter by a minute angle from the distal end to the proximal end in the axial direction.

An outer diameter $\phi$ of the first section 311 around the axis in a case where the outer peripheral surface S1 is a cylindrical shape, or an outer diameter $\phi$ of the distal end of the first section 311 in a case where the outer peripheral surface is a tapered shape, is preferably smaller than an outer diameter of the needle 21.

For example, the outer diameter $\phi$ of the first section 311 is smaller than 0.82 mm in a case where the needle 21 is made of 21G metal (outer diameter of the needle 21 is 0.82 mm), and is smaller than 0.84 mm in a case where the needle 21 is a 21G plastic trocar (outer diameter of the needle 21 is 0.84 mm).

In addition, the outer diameter $\phi$ 4 is smaller than 1.00 mm in a case where the needle 21 is made of 20G metal (outer diameter of the needle 21 is 1.00 mm), and is smaller than 1.02 mm in a case where the needle 21 is a 20G plastic trocar (outer diameter of the needle 21 is 1.02 mm).

An angle $\alpha 2$ may be larger than the angle $\alpha 1$ and is not particularly limited. The angle $\alpha 2$ is, for example, 20° to 30°. The outer peripheral surface S2 of the second section 312 has a tapered shape inclined so as to expand in diameter by the angle $\alpha 2$ from the distal end towards the proximal end in the axial direction.

Figure 5:
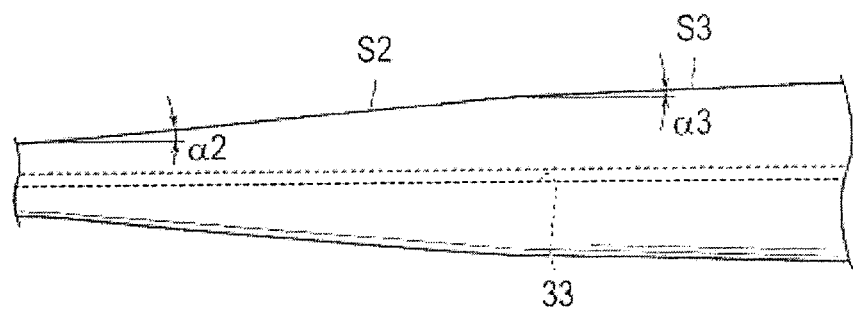
FIG. 5 is a partially enlarged view of a dilator.

In addition, as shown in FIG. 5, the angle $\alpha 2$ is larger than an angle $\alpha 3$ formed by the outer peripheral surface S3 of the third section 313 with respect to the axial direction ($\alpha 2 > \alpha 3$). The angle $\alpha 3$ is preferably 0° to 10° and more preferably 5° to 10°. In a case where the angle $\alpha 3$ is 0°, the outer peripheral surface S3 has a cylindrical shape having a constant diameter in the axial direction. In addition, in a case where the angle $\alpha 3$ is larger than 0°, the outer peripheral surface S3 has a tapered shape inclined so as to expand in diameter by a minute angle from the distal end to the proximal end in the axial direction.

Figure 6:
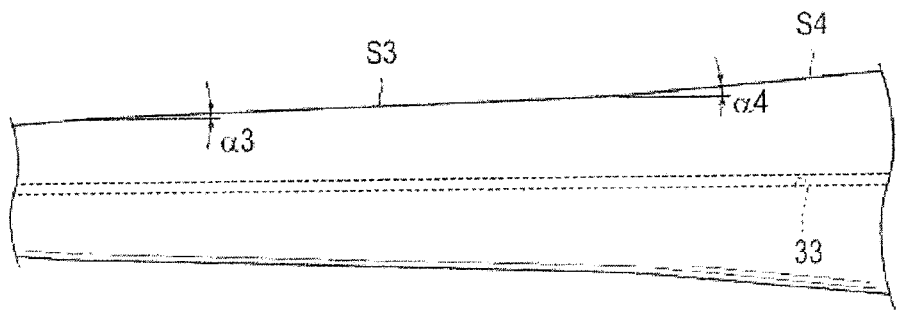
FIG. 6 is a partially enlarged view of a dilator.

As shown in FIG. 6, the angle $\alpha 3$ is smaller than an angle $\alpha 4$ formed by the outer peripheral surface S4 of the fourth section 314 with respect to the axial direction ($\alpha 3 < \alpha 4$). The angle $\alpha 4$ may be larger than the angle $\alpha 3$ and is not particularly limited. The angle $\alpha 4$ is, for example, 20° to 30°. The outer peripheral surface S4 has a tapered shape inclined so as to expand in diameter by the angle $\alpha 4$ from the distal end towards the proximal end in the axial direction.

The first section 311 and the second section 312, the second section 312 and the third section 313, and the third section 313 and the fourth section 314 are connected to each other by curved surfaces, respectively. Accordingly, a rapid change in the inclination of the outer peripheral surface along the axial direction is suppressed and the inclination of the outer peripheral surface of the dilator 30 with respect to the axial direction gently changes from the distal end towards the proximal end in the axial direction, compared to a case where the outer peripheral surfaces on the boundary of each section intersect with each other to form a circular intersecting line around the shaft center.

Next, a method of use of the medical tool 10 and a diameter expanding method of the hole by the dilator 30 will be described. These methods are performed when inserting a catheter or the like into a living body by a Seldinger method. Hereinafter, the insertion of the catheter into a blood vessel will be described as an example.

First, an operator opens the package 61 to extract the puncture tool 20. Then, the operator punctures a leg or an arm of a patient with the puncture tool 20, to form a hole which communicates the outside with the inside of the blood vessel. If the needle 21 is inserted into the blood vessel, the blood passes through the needle 21 and the hub 22 and flows into the syringe 23, and accordingly the operator can grasp whether or not the needle 21 is inserted into the blood vessel by visually recognizing the inside of the syringe 23.

After confirming the insertion of the needle 21 into the blood vessel, the operator extracts the syringe 23 from the hub 22 while maintaining the insertion of the needle 21. The operator can remove the syringe 23 from the hub 22 by pulling the syringe 23 to the proximal end side in the axial direction. In addition, a hemostatic property after extracting the syringe 23 is secured by a hemostasis valve provided in the hub 22.

After extracting the syringe 23, the operator inserts a guide wire into the blood vessel through the hub 22 and the needle 21. After that, the operator extracts the needle 21 from the patient while inserting the guide wire into the blood vessel. After extracting the needle 21, the operator inserts the dilator 30 into the hole along with the guide wire, to expand the diameter of the hole.

Figure 7:
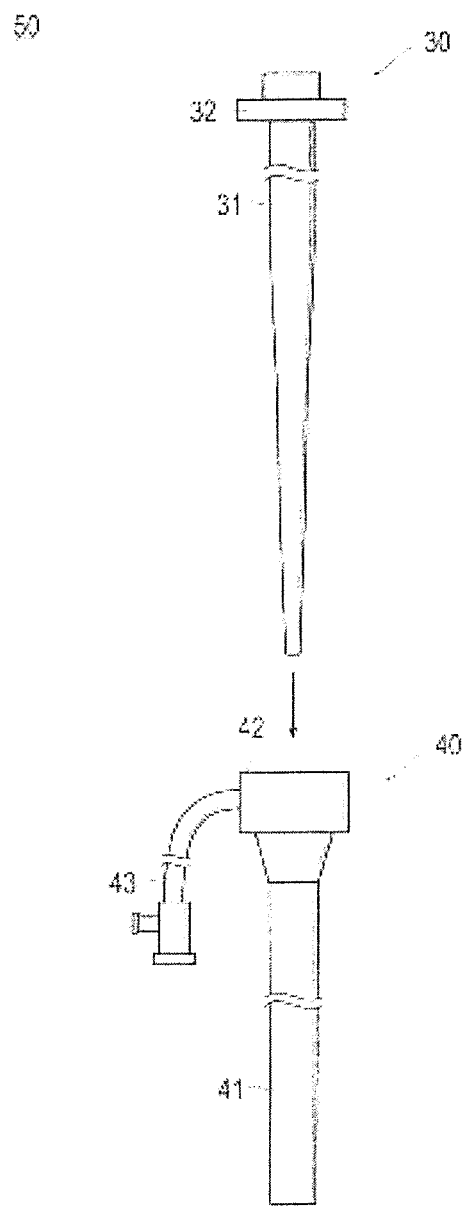
FIG. 7 is a schematic configuration diagram separately showing a dilator and an introducer sheath.
Figure 8:
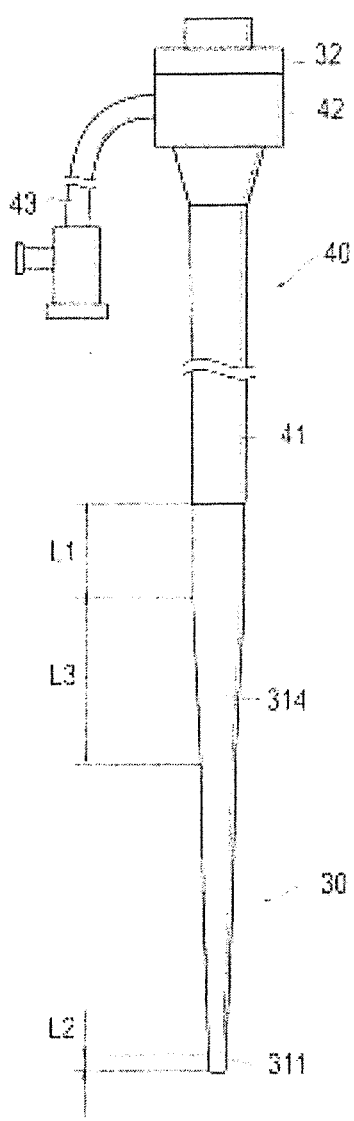
FIG. 8 is a schematic configuration diagram showing combination of a dilator and an introducer sheath.

As shown in FIG. 7 and FIG. 8, the operator inserts the dilator 30 with the introducer sheath 40 into the hole, in a state where the dilator 30 has been inserted into the introducer sheath 40 and both of them have been fixed by the dilator hub 32 and the sheath hub 42. At that time, the operator makes the guide wire pass through an inner cavity 33 to insert the introducer sheath 40 and the dilator 30 into the hole with the guide wire.

Since the dilator hub 32 is fixed to the sheath hub 42 and the outer diameter of the dilator tube 31 on the proximal end side with respect to the fourth section 314 is larger than the inner diameter of the distal end of the sheath tube 41, extraction of the dilator 30 from the distal end of the sheath tube 41 is prevented.

When the dilator 30 is inserted into the introducer sheath 40 and both of them are fixed to each other, the distal portion of the introducer sheath 40 is positioned on the proximal end side with respect to the fourth section 314 of the dilator 30, as illustrated in FIG. 8.

In addition, in this state, a length L1 from the distal endmost portion of the introducer sheath 40 to the proximal end of the fourth section 314 is greater than a length L2 of the first section and smaller than a length L3 of the fourth section (L2<L1<L3).

The dilator 30 passes through the hole and expands the diameter of the hole in a stepwise manner by the first section 311, the second section 312, the third section 313, and the fourth section 314, in this order. After the fourth section 314 passes through the hole, the distal portion of the sheath tube 41 followed by the fourth section 314 passes through the hole, and the sheath tube 41 enters into the blood vessel.

After the operator inserts a desired length of the sheath tube 41 into the blood vessel, the dilator 30 is extracted while keeping the sheath tube 41 in the blood vessel. The introducer sheath 40 is placed in the living body in a state where the proximal end remains outside of the body to exhibit a function of communicating the inside and the outside of the living body. The operator introduces a treatment tool such as a guide wire and a catheter into the living body through the introducer sheath 40 placed as described above.

According to the dilator 30 of the embodiment, the increase in the diameter expansion resistance changes in a stepwise manner in an order of relatively small, large, small, large increase, with the insertion of the dilator 30 into the hole, due to the differences in angles formed by the outer peripheral surface of each section with respect to the axial direction. Accordingly, the diameter expansion resistance sensed by the operator is alleviated and thus the insertion of the dilator 30 can be smoothly performed.

In addition, since the puncture resistance at the time when the dilator 30 punctures the hole is decreased by the outer periphery of the distal endmost portion 310 containing a parabola R, the insertion of the dilator 30 into the hole can be smoothly performed.

In addition, the outer diameter φ of the first section 311 is smaller than the outer diameter of the needle 21, and as a result, the puncture resistance at the time when the dilator 30 punctures the hole is decreased, and accordingly the insertion of the dilator 30 can be smoothly performed.

The first section 311 and the second section 312, the second section 312 and the third section 313, and the third section 313 and the fourth section 314 are connected to each other by curved surfaces, respectively, and accordingly the inclination of the outer peripheral surface of the dilator 30 with respect to the axial direction gently changes from the distal end towards the proximal end in the axial direction. As a result, resistance generated in a boundary of each section due to differences in inclination of the outer peripheral surface of each section is decreased, and accordingly the insertion of the dilator 30 can be smoothly performed.

Since the introducer assembly 50 and the medical tool 10 include the dilator 30, the same effect as the dilator 30 described above is realized.

In the introducer assembly 50, since the length L1 from the distal endmost portion of the introducer sheath 40 to the proximal end of the fourth section 314 is greater than the length L2 of the first section and is smaller than the length L3 of the fourth section (L2<L1<L3), the insertion resistance felt by the hand when the introducer sheath 40 is inserted is reduced.

In the medical tool 10, since the needle 20 and the dilator 30 are accommodated in the package 61, the operator does not need to prepare the needle 20 and the dilator 30 separately, and thus an excellent working property is obtained.

EXAMPLE

A dilator configured as described above was created and a dilator in which the increase in the diameter expansion resistance when inserting into the hole did not relatively change, that is, angles formed by each outer peripheral surface of the first section, the second section, the third section, and the fourth section with respect to the axial direction were constant, was created as a comparison target (Comparative Example). In both dilators, the main configurations other than the first section, the second section, the third section, and the fourth section were the same as each other. The dilators were obliquely inserted into a hole formed in a puncture model, using a puncture model including a blood vessel under the skin, and changes in force applied to the dilators at that time were measured. In this measurement, a sense of resistance (diameter expansion resistance) sensed by an operator at the time of insertion was examined, when the operator inserted the dilator into the hole up to the fourth section.

When the dilator configured as described above and the dilator of the Comparative Example were compared, the resistance sensed by the operator at the time of insertion was small when using the dilator configured as described above. From this result, it was found that the resistance sensed by the operator at the time of insertion is decreased, by the embodiment, that is, the configuration of including the first section, the second section, the third section, and the fourth section which have different diameters from each other and are formed to be adjacent to each other in an axial direction, in that order from a distal end to a proximal end in the axial direction, in which the angle formed by the outer peripheral surface of the first section with respect to the axial direction is smaller than the angle formed by the outer peripheral surface of the second section with respect to the axial direction, the angle formed by the outer peripheral surface of the second section with respect to the axial direction is larger than the angle formed by the outer peripheral surface of the third section with respect to the axial direction, and the angle formed by the outer peripheral surface of the third section with respect to the axial direction is smaller than the angle formed by the outer peripheral surface of the fourth section with respect to the axial direction.

The present invention is not limited to the embodiment described above, and various modifications can be performed within a scope of the claims. For example, the number of the sections having different angles formed by the outer peripheral surfaces with respect to the axial direction is not limited to four, and a fifth section in which the outer peripheral surface expands the diameter in a tapered shape may be further provided at the proximal end side of the fourth section of the embodiment.

The detailed description above describes a dilator, introducer assembly, and medical tool. The dilator, introducer assembly, and medical tool are disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A dilator comprising a first section, a second section, a third section, and a fourth section which have different diameters from each other and are formed to be unitary with and adjacent to each other in an axial direction,
    wherein the first section is adjacent to and disposed on a distal side of the second section, the second section is adjacent to and disposed on a distal side of the third section, and the third section is adjacent to and disposed on a distal side of the fourth section,
    an angle $\alpha 1$ formed by an outer peripheral surface of the first section with respect to the axial direction is smaller than an angle $\alpha 2$ formed by an outer peripheral surface of the second section with respect to the axial direction,
    the angle $\alpha 2$ formed by the outer peripheral surface of the second section with respect to the axial direction is larger than an angle $\alpha 3$ formed by an outer peripheral surface of the third section with respect to the axial direction,
    the angle $\alpha 3$ formed by the outer peripheral surface of the third section with respect to the axial direction is smaller than an angle $\alpha 4$ formed by an outer peripheral surface of the fourth section with respect to the axial direction,
    the outer peripheral surface of the first section has a tapered shape so as to expand in diameter by the angle $\alpha 1$ from the distal end towards the proximal end in the axial direction,
    the outer peripheral surface of the second section has a tapered shape so as to expand in diameter by the angle $\alpha 2$ from the distal end towards the proximal end in the axial direction,
    the outer peripheral surface of the third section has a tapered shape so as to expand in diameter by the angle $\alpha 3$ from the distal end towards the proximal end in the axial direction, and
    the outer peripheral surface of the fourth section has a tapered shape so as to expand in diameter by the angle $\alpha 4$ from the distal end towards the proximal end in the axial direction.

2. The dilator according to claim 1, further comprising a distal portion which is formed on a distal end side of the first section in the axial direction,
    wherein an outer periphery of the distal portion in a cross section in the axial direction which passes through a shaft center includes a parabola in which a diameter thereof decreases towards a distal end from a proximal end in the axial direction, and which has a convex shape from the shaft center towards the outer side in a radial direction.

3. The dilator according to claim 1, wherein the first section and the second section, the second section and the third section, and the third section and the fourth section are connected to each other by curved surfaces, respectively.

4. The dilator according to claim 2, wherein the first section and the second section, the second section and the third section, and the third section and the fourth section are connected to each other by curved surfaces, respectively.

5. An introducer assembly comprising:
    a dilator which includes a first section, a second section, a third section, and a fourth section which have different diameters from each other and are formed to be unitary with and adjacent to each other in an axial direction; and
    an introducer sheath which includes a lumen into which the dilator can be inserted and a distal portion,
    wherein the first section is adjacent to and disposed on a distal side of the second section, the second section is adjacent to and disposed on a distal side of the third section, and the third section is adjacent to and disposed on a distal side of the fourth section,
    an angle $\alpha 1$ formed by an outer peripheral surface of the first section with respect to the axial direction is smaller than an angle $\alpha 2$ formed by an outer peripheral surface of the second section with respect to the axial direction,
    the angle $\alpha 2$ formed by the outer peripheral surface of the second section with respect to the axial direction is larger than an angle $\alpha 3$ formed by an outer peripheral surface of the third section with respect to the axial direction,
    the angle $\alpha 3$ formed by the outer peripheral surface of the third section with respect to the axial direction is smaller than an angle $\alpha 4$ formed by an outer peripheral surface of the fourth section with respect to the axial direction,
    the outer peripheral surface of the first section has a tapered shape so as to expand in diameter by the angle $\alpha 1$ from the distal end towards the proximal end in the axial direction,
    the outer peripheral surface of the second section has a tapered shape so as to expand in diameter by the angle $\alpha 2$ from the distal end towards the proximal end in the axial direction,
    the outer peripheral surface of the third section has a tapered shape so as to expand in diameter by the angle $\alpha 3$ from the distal end towards the proximal end in the axial direction,
    the outer peripheral surface of the fourth section has a tapered shape so as to expand in diameter by the angle $\alpha 4$ from the distal end towards the proximal end in the axial direction, and
    the distal portion of the introducer sheath is disposed at a proximal end side with respect to a proximal end of the fourth section.

6. The introducer assembly according to claim 5, wherein a length from a distal endmost portion of the distal portion of the introducer sheath to the proximal end of the fourth section of the dilator is greater than a length of the first section of the dilator and smaller than a length of the fourth section of the dilator.

7. The introducer assembly according to claim 5, wherein the first section and the second section, the second section and the third section, and the third section and the fourth section are connected to each other by curved surfaces, respectively.

8. The introducer assembly according to claim 6, wherein the first section and the second section, the second section and the third section, and the third section and the fourth section are connected to each other by curved surfaces, respectively.

9. A medical tool comprising:
a dilator which includes a first section, a second section, a third section, and a fourth section which have different diameters from each other and are formed to be unitary with and adjacent to each other in an axial direction; and
a needle which can form a hole communicating with a body lumen, by puncturing the skin,
wherein the first section is adjacent to and disposed on a distal side of the second section, the second section is adjacent to and disposed on a distal side of the third section, and the third section is adjacent to and disposed on a distal side of the fourth section,
an outer diameter of the first section is smaller than an outer diameter of the needle,
an angle $\alpha 1$ formed by an outer peripheral surface of the first section with respect to the axial direction is smaller than an angle $\alpha 2$ formed by an outer peripheral surface of the second section with respect to the axial direction,
the angle $\alpha 2$ formed by the outer peripheral surface of the second section with respect to the axial direction is larger than an angle $\alpha 3$ formed by an outer peripheral surface of the third section with respect to the axial direction,
the angle $\alpha 3$ formed by the outer peripheral surface of the third section with respect to the axial direction is smaller than an angle $\alpha 4$ formed by an outer peripheral surface of the fourth section with respect to the axial direction,
the outer peripheral surface of the first section has a tapered shape so as to expand in diameter by the angle $\alpha 1$ from the distal end towards the proximal end in the axial direction,
the outer peripheral surface of the second section has a tapered shape so as to expand in diameter by the angle $\alpha 2$ from the distal end towards the proximal end in the axial direction,
the outer peripheral surface of the third section has a tapered shape so as to expand in diameter by the angle $\alpha 3$ from the distal end towards the proximal end in the axial direction, and
the outer peripheral surface of the fourth section has a tapered shape so as to expand in diameter by the angle $\alpha 4$ from the distal end towards the proximal end in the axial direction.

10. The medical tool according to claim 9, wherein the needle and the dilator are accommodated in one package.

11. The medical tool according to claim 9, wherein the first section and the second section, the second section and the third section, and the third section and the fourth section are connected to each other by curved surfaces, respectively.

12. The medical tool according to claim 10, wherein the first section and the second section, the second section and the third section, and the third section and the fourth section are connected to each other by curved surfaces, respectively.

13. The dilator according to claim 1, wherein the dilator defines a lumen through the first section, the second section, the third section and the fourth section.

14. The introducer assembly according to claim 5, wherein the dilator defines a lumen through the first section, the second section, the third section and the fourth section.

15. The medical tool according to claim 9, wherein the dilator defines a lumen through the first section, the second section, the third section and the fourth section.

* * * * *